US012751856B2

United States Patent
Dunlop et al.

(10) Patent No.: US 12,751,856 B2
(45) Date of Patent: Oct. 6, 2026

(54) PATIENT WARMING BLANKET

(71) Applicants: Colin Dunlop, East Ryde (AU); James Dunlop, Gladesville (AU)

(72) Inventors: Colin Dunlop, East Ryde (AU); James Dunlop, Gladesville (AU)

( * ) Notice: Subject to any disclaimer, the term of this patent is extended or adjusted under 35 U.S.C. 154(b) by 1013 days.

(21) Appl. No.: 16/767,490

(22) PCT Filed: Nov. 27, 2018

(86) PCT No.: PCT/AU2018/051260
§ 371 (c)(1),
(2) Date: May 27, 2020

(87) PCT Pub. No.: WO2019/104376
PCT Pub. Date: Jun. 6, 2019

(65) Prior Publication Data

US 2020/0375794 A1 Dec. 3, 2020

(30) Foreign Application Priority Data

Nov. 28, 2017 (AU) ................................ 2017904805

(51) Int. Cl.
*A61F 7/02* (2006.01)
*A61F 7/00* (2006.01)

(52) U.S. Cl.
CPC .............. *A61F 7/0097* (2013.01); *A61F 7/02* (2013.01); *A61F 2007/006* (2013.01); *A61F 2007/0091* (2013.01); *A61F 2007/0274* (2013.01)

(58) Field of Classification Search
CPC .... A61F 7/0097; A61F 7/02; A61F 2007/006; A61F 2007/0091; A61F 2007/0274
See application file for complete search history.

(56) References Cited

U.S. PATENT DOCUMENTS

| | | | |
|---|---|---|---|
| 4,660,388 | A | 4/1987 | Greene, Jr. |
| 5,165,400 | A | 11/1992 | Berke |
| 5,300,102 | A | 4/1994 | Augustine |
| 5,405,370 | A | 4/1995 | Irani |

(Continued)

FOREIGN PATENT DOCUMENTS

WO 2004052250 A1 6/2004

OTHER PUBLICATIONS

International Search Report dated Apr. 3, 2019 for corresponding International Application No. PCT/AU2018/051260.

*Primary Examiner* — Michael F Peffley
*Assistant Examiner* — Bo Ouyang
(74) *Attorney, Agent, or Firm* — Tarolli, Sundheim, Covell & Tummino LLP

(57) ABSTRACT

A patient warming blanket comprising at least two layers capable of forming a hollow air space between the two layers for receiving warm air from a heating unit via an inlet port at or near an end of the blanket. The two layers being arranged so that the hollow air space forms at least one tubular portion disposed longitudinally there within, and one of the two layers has at least a portion of its surface formed of porous material so that warmed air is delivered to said patient by diffusion through said porous material. The tubular portion has non-parallel sides such that the sides of the tubular portion are further apart from each other at a first end of the tubular portion closer to the inlet port than at a second end of the tubular portion remote from the inlet port.

7 Claims, 6 Drawing Sheets

(56) References Cited

U.S. PATENT DOCUMENTS

| | | | | |
|---|---|---|---|---|
| 6,277,144 | B1 | 8/2001 | Tomic-Edgar | |
| 6,354,099 | B1 * | 3/2002 | Bieberich | A61F 7/10<br>607/104 |
| 2010/0211138 | A1 | 8/2010 | Pierre | |
| 2011/0098792 | A1 * | 4/2011 | Lowe | A61F 7/0085<br>607/104 |
| 2012/0079656 | A1 * | 4/2012 | Lewis | A61F 7/00<br>5/81.1 R |
| 2016/0374852 | A1 * | 12/2016 | Kane | A61H 9/00<br>156/275.1 |
| 2017/0313021 | A1 * | 11/2017 | Chakravarty | B32B 27/308 |

* cited by examiner

PATIENT WARMING BLANKET

RELATED APPLICATIONS

The present application is a U.S. National Stage application under 35 USC 371 of PCT Application Serial No. PCT/AU2018/051260, filed on 27 Nov. 2018; which claims priority from AU patent application No. 2017904805, filed 28 Nov. 2017, the entirety of both of which are incorporated herein by reference.

TECHNICAL FIELD

This invention relates to a patient warming blanket. In particular the present invention is described with reference to a patient warming blanket for use in veterinary care.

BACKGROUND

Prior to 2002 the most common forced warm air patient blankets were large enough to lay over human beings lying on a bed, and some of these were marketed as BAIR HUGGER™ (originally by Augustine Medical and now by 3M) and WARM TOUCH™ (by Mallinckrodt), and by Cincinnati Sub Zero. Initially such blankets were intended to warm human beings recovering from anaesthesia. However, human patients would normally warm physiologically through shivering, vasoconstriction, and increased cardiac function as the person returned to the normal un-anaesthetised state. As such, there was minimal evidence to suggest these warm air blankets were particularly effective.

These early type of blankets for human use were constructed from two layers of material sewn or bonded together in such a way to create air channels (tubular pillows) on inflation similar to an air mattress. The blanket is inflated using a warm air blower unit (heater) with large enough air flow to be matched to their size. Originally these blankets were made of washable material, and then of disposable material, with air permeability provided by 1 mm to 2 mm holes disposed about 0.5 cm to 1 cm apart across the layer on the patient contact side. The intent of the holes was to allow warm air introduced into the blanket to "jet downwards" towards the patient.

In time these blankets were designed to be laid over the top of humans during surgery, and because body parts needed to be exposed to the surgeon, some smaller blanket designs were developed as half-torso blankets, which were also suitable for use in smaller human infants and neonates.

Adult humans have a large body mass and relatively small surface area so their loss of body heat and risk of hypothermia is lower than that of infants/neonates, so flowing warm air across the skin of an adult patient can effectively warm the adult patient. Originally, half-sized adult human blankets with warm air blower units were used on infants/neonates. If the blanket size was too small, the air flow generated by the warm air blower unit would increase through the punched holes creating more air movement over the skin surface in a wind tunnel effect, potentially causing a cooling effect rather than the intended warming. Unlike adult humans, infants and neonates have a small body mass and relatively larger surface area. This combined with the fact that a larger proportion of skin surface of an infant/neonate is exposed during surgery, with limited blanket contact area for surface warming by the blanket, meant warming for an infant/neonate was not as effective as in adult humans.

Over 80% of anaesthetized dogs and cats are smaller than 15 kg and many smaller than 5 kg. Like that of infants/neonates, their small body mass relative to large body surface area makes them prone to severe hypothermia (temperature rapidly falling to 32° C.). In 1995 at Colorado State University the present inventor (with others) trialled human infant blankets by BAIR HUGGER™ laid over the top of 3-5 kg cats and dogs during surgery and recovery from anaesthesia. However, the excessive air flow from these smaller blankets jetting downward over the small animal with a large surface area relative to body weight, failed to provide an effective warming effect, but instead caused cooling. This finding was also observed in other trials at University Of Minnesota, see "Warming with a forced air warming blanket minimizes anesthetic-induced hypothermia in cats" by Machon R G, Raffe M R & Robinson E P, published in Veterinary Surgery Volume 28, Issue 4, July 1999 Pages 301-310.

Other warming devices for human patients during surgery and recovery involve U-shaped hollow bodies (tubular pillows) as disclosed in U.S. Pat. No. 5,165,400 (Berke) and U.S. Pat. No. 6,277,144 (Tomic-Edgar et, al). In both these devices the U-shaped tubular pillows have a plurality of orifices (holes) so that warm air blown into the pillows can be delivered to the patient.

As human patient over the top blanket technology was not particularly effective in warming of hypothermic cats and dogs from the start of anaesthesia through to surgery, a blanket suitable for animals was developed over a number of years. Initially a U-shaped blanket was developed and improved on, resulting in a U-shaped blanket as shown in embodiments of International Patent publication No. WO2004/052250 (Dunlop). The blanket was made with two polyester layers (upper and lower layers) bonded together, so that a U-shaped hollow air space is adapted to receive warm air and inflate, with the lower layer substantially non-porous and the upper layer substantially porous over its entire surface area. The initial U-shaped blanket for dogs were designed to suit medium to larger dogs both in its patient receiving area and the height of the blanket. The height of the surrounding blanket was importantly kept at a height to not obstruct the surgery or interfere with surgical drapes. The effectiveness of such U-shaped blanket for a medium to large dog was proven in research conducted at the University of Sydney, see Lau A Dart C (supervisor) "*Effectiveness of a forced warm air blanket in correcting hypothermia during general anaesthesia in dogs*" Honours Thesis 0420964: The University of Sydney Library; 2008. However, these blankets designed for medium to large dogs were found to not be as effective in warming smaller dogs and cats, and were too high for surgery of the smaller animals, because when inflated they were elevating the surgical drapes above the animal. As such a smaller U-shaped blanket was developed for smaller dogs and cats having a tighter curve at the U-shape and a lower profile when inflated.

Further developments have led to various U-shaped blankets, tube blankets and over blankets designed to suit various sized animals and the configuration of their recovery cages, so that they can be warmed during the post-operative recovery. This is achieved by a cage door adaptor mechanism allowing for the duct from the warm air blower unit outside the cage to engage with ducting inside the cage that delivers warm air to the blanket, as disclosed in International Patent publication No. WO2010/111750 (Dunlop).

In all of these abovementioned prior art blanket designs, including the over the top human patient blankets, and U-shaped blankets and other known tube "wrap around" blankets, the "elongate tubular pillow" or longitudinal air pockets (or spaces) are based on conventional air mattress design, where each tubular air pillow or tubular air pocket (or space) has substantially parallel longitudinal sides.

A recent trial was undertaken utilizing infrared technology to evaluate the efficacy of various prior art warming blankets and heaters used to heat animals during surgery and recovery. In addition to the infrared imaging finding rapid temperature drops in the initial ducting leaving the heater, there was:

- poor distribution of warm air at the blanket inlet port bends;
- poor distribution of warm air around tight bends and/or where it kinks;
- where inlet is to one side of blanket, there is poor distribution to tubular air pockets on far side of blanket; and
- the porosity of blanket material affects distribution of air flow.

The present invention is to provide a patient blanket that overcomes at least one of the problems associated with the prior art.

SUMMARY OF INVENTION

In a first aspect the present invention consists of a patient warming blanket comprising at least two layers capable of forming a hollow air space between said two layers for receiving warm air from a heating unit via an inlet port at or near an end of said blanket, said two layers being arranged so that said hollow air space forms at least one tubular portion disposed longitudinally within said blanket, and one of said two layers has at least a portion of its surface formed of porous material so that warmed air is delivered to said patient by diffusion through said porous material, wherein said tubular portion has non-parallel sides such that said sides of said tubular portion are further apart from each other at a first end of said tubular portion closer to said inlet port than at a second end of said tubular portion remote from said inlet port.

Preferably said at least one tubular portion comprises a plurality of tubular portions fluidally in communication with each other.

Preferably said plurality of tubular portions are disposed longitudinally adjacent to each other, and a manifold is disposed between said inlet port and said first ends of said tubular portions.

Preferably said manifold has a length which is no less than twenty percent the total length of said blanket.

Preferably said first ends of said tubular portions are staggered relative to each other.

Preferably said staggered first ends of said tubular portions are staggered such that centrally disposed tubular portions have first ends longitudinally further away from said inlet port than adjacent tubular portions disposed on either side thereof.

Preferably a gallery is disposed at a bottom end of said blanket near said second ends of said tubular portions and said gallery is in fluid communication with said gallery, and said gallery has a width between said bottom end and said second ends of said tubular portions which is no less than ten percent the total length of said blanket.

Preferably at least one of the outermost tubular portions is about ten percent larger than an adjacent tubular portion.

Preferably said two layers are welded together such that said hollow space is substantially surrounded by a peripheral weld.

Preferably an external weld at least partially surrounds said peripheral weld.

In a second aspect the present invention consists of a patient warming blanket comprising at least two layers capable of forming a hollow air space between said two layers for receiving warm air from a heating unit via an inlet port at or near an end of said blanket, said two layers being arranged so that said hollow air space comprises a plurality of adjacent tubular portions disposed longitudinally within said blanket and fluidally in communication with each other via a manifold at said first ends of said tubular portions near said inlet port and a gallery at the opposed ends of said tubular portions, and one of said two layers has at least a portion of its surface formed of porous material so that warmed air is delivered to said patient by diffusion through said porous material, wherein said tubular portions have non-parallel sides such that said sides of said tubular portions are further apart from each other at their first ends nearer to said inlet port than at said opposed ends of said tubular portion near said gallery.

Preferably said manifold has a length which is no less than twenty percent the total length of said blanket.

Preferably said first ends of said tubular portions are staggered relative to each other such that centrally disposed tubular portions have first ends longitudinally further away from said inlet port than adjacent tubular portions disposed on either side thereof.

Preferably said gallery has a width between said bottom end of said blanket and said opposed ends of said tubular portions which is no less than ten percent the total length of said blanket.

Preferably at least one of the outermost tubular portions is about ten percent larger than an adjacent tubular portion.

Preferably said two layers are welded together such that said hollow space is substantially surrounded by a peripheral weld.

Preferably an external weld substantially surrounds said peripheral weld.

In a third aspect the present invention consists of a patient warming blanket comprising at least two layers capable of forming a hollow air space between said two layers for receiving warm air from a heating unit via an inlet port at or near an end of said blanket, said two layers being arranged so that said hollow air space is U-shaped and comprising first and second elongate tubular portions fluidally connected by a tubular bend portion, and one of said two layers has at least a portion of its surface formed of porous material so that warmed air is delivered to said patient by diffusion through said porous material, said first elongate tubular portion having an inlet and associated manifold at its free end, wherein said first tubular portion has non-parallel sides such that said sides of said first tubular portion are further apart from each other at a first end of said tubular portion closer to said inlet port than at a second end of said tubular portion near said tubular bend.

Preferably said second tubular portion has non-parallel sides such that said sides of said second tubular portion are further closer together at an end of said second tubular portion closer to said tubular bend portion than at a second end of said second tubular portion near its closed free end.

BEST MODE OF CARRYING OUT THE INVENTION

Figure 1:
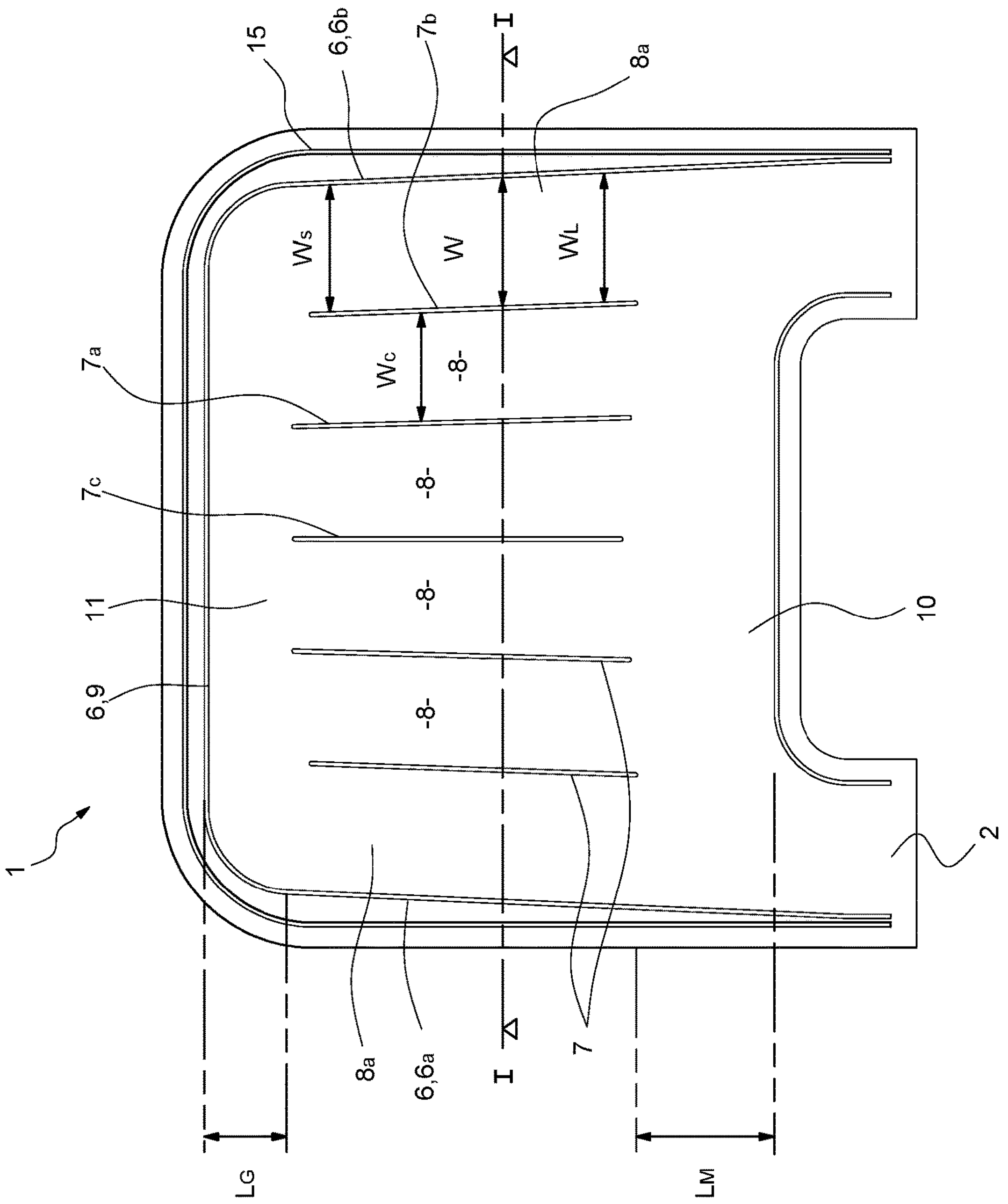
FIG. 1 is a plan view of a single cage animal patient blanket in a first embodiment of the present invention.
Figure 2:
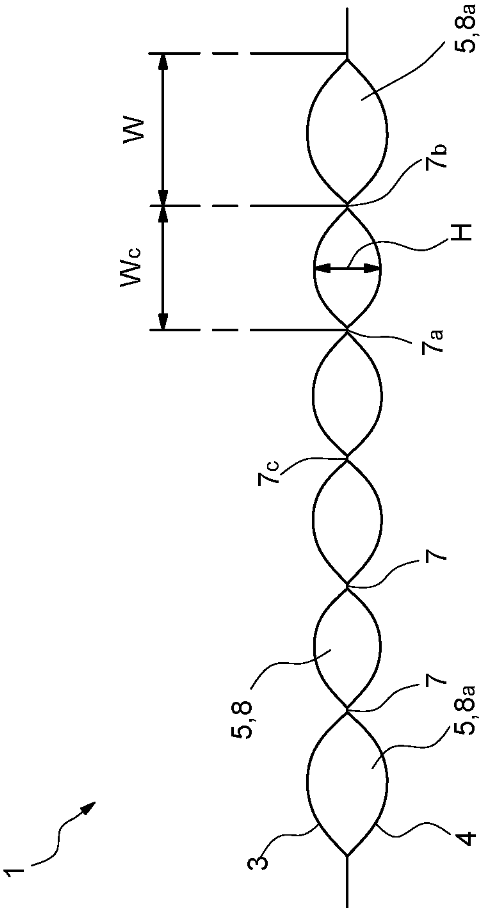
FIG. 2. is a cross-section through I-I on FIG. 1.

FIGS. 1 and 2 depict a first embodiment of a blanket 1 which is for use in veterinary medicine, and suited for being placed in a single animal cage for post operative warming of cat or small dog patient. Blanket 1 is in use connected to a blower heating unit (not shown), via an inlet 2.

Blanket 1 is made of two layers, a first layer 3 and a second layer 4, which form a hollow air space 5 between them. When blanket 1 is not being used it will lie substantially flat as no air is being introduced into air space 5. In, use however, when warm air is being blown into air space 5, blanket 1 inflates to give a profile shown in cross-section of FIG. 2.

First layer 3 is made of a substantially non-porous material, whilst second layer 4 is made of a porous material. Whilst blanket 1 may be made of any appropriate thin material, in this embodiment it is made of polyester, with upper layer 4 being of porous polyester.

The purpose of the porous second layer 4 is to allow warm air introduced into hollow space 5 to gently diffuse there through at low velocity for warming the patient (not shown).

In manufacture of blanket 1, layers 3,4 are heat welded together to form a periphery 6, and a plurality of elongate "continuous" welds 7 are disposed spaced apart to form a plurality of elongate tubular portions 8, 8*a* of hollow air space 5 adjacent to each other. Periphery 6 is the peripheral weld substantially surrounding the portion of blanket 1 to be inflated. Welds 7, also applied by heat do not extend the full length of blanket 1, and therefore in use air entering blanket 1 can enter tubular portions 8,8*a* from either end.

Welds 7 together with the peripheral edges 6*a*,6*b* of hollow space 5 form "sides" of tubular portions 8, 8*a*. However, it should be pointed out that the sides defined by welds 7 and peripheral edges 6*a*,6*b* are non-parallel (or tapered), such that the tubular portions 8, 8*a* each have wider openings at location nearer inlet 2 than they do near the opposed closed end 9 of blanket 1. In this embodiment the centrally disposed weld (side) 7*c* is substantially parallel to the longitudinal axis of blanket 1. The peripheral edges 6*a*,6*b* are skewed at two and a half (2.5) degrees to side 7*c*, and side 7*a* is skewed at one and a half (1.5) degrees to the side 7*c*, whilst side 7*b* is skewed at about two degrees to the side 7*c*.

The two opposed outermost tubular portions 8*a* have a width W that is about ten percent wider than width $W_C$ of tubular portions 8, disposed between them.

By looking at the cross-section of FIG. 2 you will see the width of a tubular portion 8*a* indicated as dimension W. As the tubular portion 8*a* has sides that are non-parallel (tapered), the width dimension $W_L$ near the inlet end of blanket 1 is larger than W at the cross-section of FIG. 2, and near the opposed end of tubular portion 8 the width dimension $W_S$ is smaller than both dimensions $W_L$ and W.

The abovementioned dimensions W, $W_L$ and $W_S$ are described with a single tubular portion 8*a*, however preferably, each tubular portion 8,8*a* has a width larger towards the inlet end of blanket 1, rather than its width nearer to closed end 9 of blanket 1. Or stated otherwise, the sides of tubular portion 8,8*a* are further apart from each other at a first end of tubular portion 8,8*a* closer to inlet port 2 than at a second end of tubular portion 8,8*a* remote from inlet port 2.

Skewing the edges and sides by just a few degrees, so that the tubular portions 8,8*a* at the inlet end are slightly larger than at the opposed closed end, markedly improves air distribution along the tubular portions 8,8*a*.

It should be noted that the cross-section of the tubular portions 8,8*a* when inflated approximate an "oval" form as shown in FIG. 2. However it is customary to refer to the tubular portions as having a "diameter", and a simplified way of correlating this oval form to a nominal calculated tube diameter, is to say that the width W of the oval form is ten percent greater than the calculated diameter, and height H is about ten percent smaller than the calculated diameter.

In an area disposed immediately between first ends of tubular portions 8,8*a* near the inlet end of the blanket towards inlet 2 is a manifold 10. The area of manifold 10 should be of a size sufficient to allow a portion of the warm air entering blanket 1 via inlet 2 on one side of blanket 1 to easily travel and reach across to the tubular portions 8,8*a* disposed furthest from inlet 2. The centrally disposed tubular portions 8 have first ends longitudinally further away from said inlet port than opposed tubular portions 8*a* disposed on either side thereof. The length $L_M$ of manifold 10 from inlet 2 to the open first ends of tubular portions 8 should preferably not be less than twenty percent of the length of the hollow space of blanket 1.

By providing manifold 10 and tubular portions 8,8*a* with non-parallel sides with wider openings near the inlet end of blanket 1, and the outermost tubular portions 8*a* being larger, at least a portion of warm air 1 being delivered to inlet 2 to inflate blanket 1 has a better opportunity to distribute evenly through tubular portions 8,8*a* and get to the opposed closed end 9. Whilst there will be heat loss as the warm air moves away from inlet 2 because of the porosity of upper layer, the abovementioned arrangement having tubular portions 8,8*a* with non-parallel sides and manifold 10 ameliorates the warm air distribution over that achievable by the prior art.

In an area disposed immediately between second ends of tubular portions 8,8*a* and the closed end 9 is a gallery 11. The area of gallery 11 should be of a size sufficient to allow a portion of the warm air passing through tubular portion 8*a* closest to inlet 2 on one side of blanket 1 to easily pass there through and travel and reach across to the second ends of tubular portions 8,8*a* disposed furthest from inlet 2. The length $L_G$ of gallery 11 between closed end 9 to the open second ends of tubular portions 8,8*a* should preferably not be less than ten percent the length of blanket 1. By doing this, along with providing a further external weld 15 disposed externally of periphery 6, minimises the possibility of kinking or other forms of restriction towards bottom end 9.

In the abovementioned first embodiment whilst the nominal calculated diameter of the tubes varies it can be estimated that tubular portions 8 when inflated are about 145 mm diameter. The blanket in this embodiment having a length (from inlet end to closed end) of about 850 mm, and a width of about 875 mm.

The manifold 10 and gallery 11 also have an oval like shape if viewed in cross section transversely rather than longitudinally ie at right angles to the longitudinal extent of the blanket. Like that of the tubular portions 8,8*a* the oval form can be expressed as a nominal calculated diameter. In this embodiment the calculated nominal diameter of manifold 10 is about 110 mm at the outlet side and expands to about 120 mm in the centre. Thus manifold 10 has a nominal diameter that varies between fifteen to twenty-five percent (about twenty percent) the nominal diameter of tubular portions 8,8*a*. Also in this embodiment the calculated nominal diameter of gallery 11 is about 65 mm.

Figure 3:
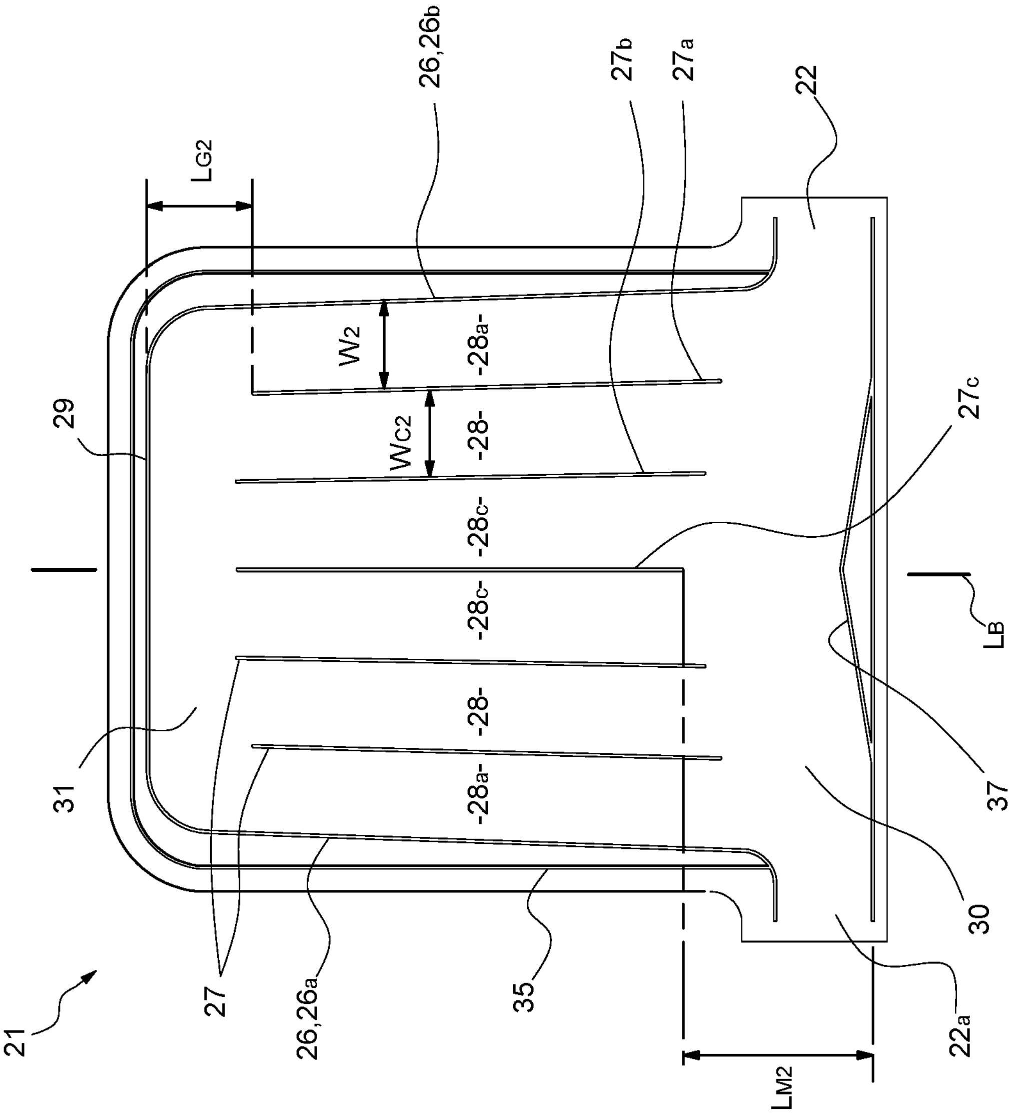
FIG. 3 is a plan view of a double cage animal patient blanket in a second embodiment of the present invention.

FIG. 3 depicts a second embodiment of a blanket 21 which also is for use in veterinary medicine, and suited for being placed in a double animal cage for post operative warming of a medium to small dog patient. Blanket 21, like blanket 1 of the first embodiment, is provided with a hollow space which in use is connected to a blower heating unit (not shown), via either inlet 22, 22*a*.

Also like blanket 1, blanket 21 is manufactured by heat welding two layers together, with the second layer being made of porous material. The periphery 26 and continuous heat welds 27 define sides of a plurality of tubular portions 28, 28*a*, and 28*c*. The sides defined by welds 27 and peripheral edges 26*a*,26*b* are non-parallel (or tapered), such that the tubular portions 28,28*a*, and 28*c* each have wider openings at a location nearer inlets 22,22*a* than they do near the opposed closed end 29 of blanket 21. In this embodiment the centrally disposed weld (side) 27*c* is substantially parallel to the longitudinal axis $L_B$ of blanket 21. Peripheral edge 26*b* is skewed at about two and a half (2.5) degrees to longitudinal axis $L_B$ and the closest side 27*a* to inlet 22 is skewed two (2) degrees to the longitudinal axis $L_B$. Side 27*b* is skewed at one and a half (1.5) degrees to the longitudinal.

Blanket 21 is also provided with a manifold 30. The centrally disposed tubular portions 28*c* have first ends longitudinally further away from inlet ports 22,22*a* than adjacent tubular portions 28 disposed on either side thereof. This provides a larger manifold area near the longitudinal axis $L_B$ of blanket 21. The length $L_{M2}$ of manifold 30 between the central open first ends of tubular portions 28 preferably should not be less than twenty percent of the length of blanket 21.

Near the inlet end of blanket 21 a chevron shaped weld 37 is centrally disposed. Weld 37 is shaped such that a portion of the air entering either inlet 22,22*a* is channeled towards the central portion of blanket 21, and in particular tubular portions 28*c*, thus assisting in air distribution.

In an area disposed immediately between second ends of tubular portions 28 and the closed end 29 is a gallery 31. The length $L_{G2}$ of gallery 31 between closed end 29 to the open second ends of tubular portions 28 should preferably not be less than ten percent of the length of blanket 21. Again like in the first embodiment, by doing this, along with providing a further external weld 35 disposed externally of periphery 26, this minimises the possibility of kinking or other forms of restriction towards bottom end 29, and therefore improves the distribution of warm air.

Manifold 30 and gallery 31 also have an oval like shape if viewed in cross section transversely rather than longitudinally ie at right angles to the longitudinal extent of the blanket. The calculated (or average) nominal diameter of manifold 30 is about 180 mm. Thus manifold 30 has a nominal diameter is one hundred percent larger (or double the size) of that of the tubular portions 28. In effect it expands over 90% between the outlet side to the centre.

The two opposed outermost tubular portions 28*a* have a nominal width W that is about ten percent wider than width $W_{C2}$ of tubular portions 8, disposed between them.

In the abovementioned second embodiment whilst the nominal calculated diameter of the tubes varies it can be estimated that tubular portions 28 when inflated are about 140 mm nominal diameter. The blanket in this embodiment having a length (from inlet end to closed end) of about 1200 mm, and a width (at inlet end) of about 1180 mm.

In approximately "rectangular" blankets such as those shown in FIGS. 1 and 3 you have at least one air inlet feeding a short, high flow reservoir, namely a manifold that distributes warm air substantially evenly to the higher resistance plurality of substantially longitudinally disposed tubular portions which feed into an end gallery, or alternatively a blind end. The manifold acts as a pressure regulator and configured to distribute the warm air as evenly as possible across the openings of the tubular portions, with the openings of some centrally disposed tubular portions being further distant from those closer to the outlet end. The nominal calculated diameter of the manifold should be no less than and preferably greater than the nominal calculated tube diameter, sufficient to accommodate airflow for all the longitudinally disposed tubular portions. In the abovementioned embodiments the average nominal calculated diameter of the manifolds 10, 30 is a minimum of about twenty percent of the length. The manifold is larger in the centrally disposed area than at the sides, thus providing a funnel or tapered shape to encourage even distribution of warm air flow to more distant openings of longitudinal tubular portions.

Figure 4:
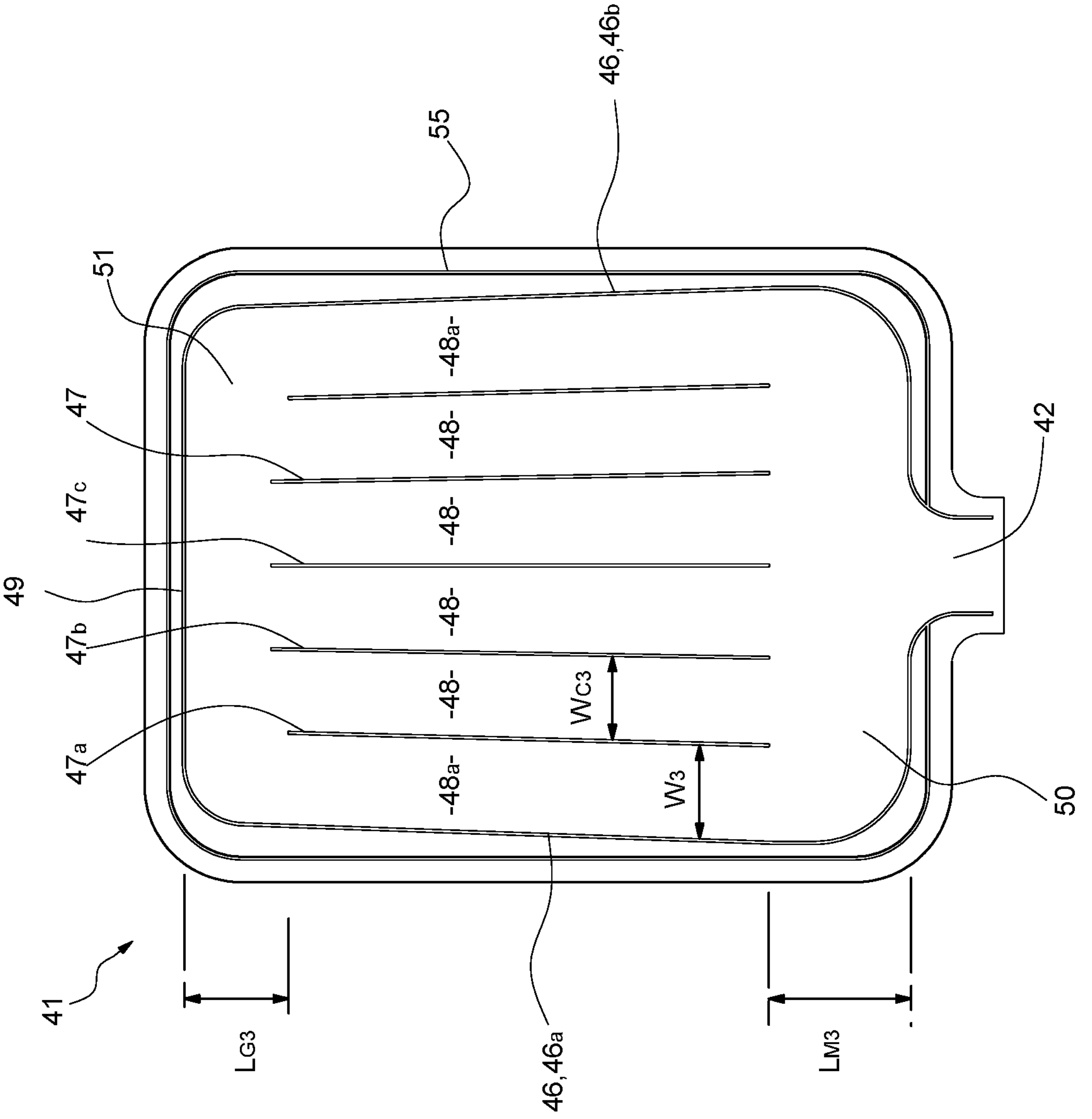
FIG. 4 is a plan view of an animal patient blanket in a third embodiment of the present invention.

FIG. 4 depicts a third embodiment of a blanket 41 which also is for veterinary medicine, and suited for surgery or recovery of a medium to large dog. Blanket 41 like that of blanket 1 is provided with a hollow space which in use is connected to a blower heating unit (not shown).

Also like blanket 1, blanket 41 is manufactured by heat welding two layers together, the second layer being made of porous material. Blanket 61 has a centrally disposed inlet 42.

The periphery 46 and heat welds 47 define sides of a plurality of tubular portions 48,48*a*,48*c*. The sides defined by welds 47 and peripheral edges 46*a*,46*b* are non-parallel (or tapered), such that the tubular portions 48,48*a*,48*c* each have wider openings at location nearer inlet 42 than they do near the opposed closed end 29 of blanket 21. In this embodiment the centrally disposed weld (side) 47*c* is substantially parallel to the longitudinal axis of blanket 41. Peripheral edge 46*a* is skewed at about two and a half (2.5) degrees to weld (side) 47*c* and side 47*a* is skewed two (2) degrees to weld (side) 47*c*. Side 47*b* is skewed at one and a half (1.5) degrees to weld (side) 47*c*.

Furthermore the two opposed outermost tubular portions 48*a* have a width $W_3$ that is about ten percent wider than the width $W_{C3}$ of tubular portions 48, disposed between them.

Blanket 41 is also provided with a manifold 50. The length $L_{M3}$ of manifold 30 between the central open first ends of tubular portions 28 preferably should not be less than 20% the length of blanket 20.

In an area disposed immediately between second ends of tubular portions 48 and the closed end 49 is a gallery 51. The length $L_{G3}$ of gallery 51 between closed end 49 to the open second ends of tubular portions 48 should preferably not be less than ten percent the length of blanket 41. Again like in the first embodiment, by doing this, along with providing a further external weld 55 disposed externally of periphery 26, minimises the possibility of kinking or other forms of restriction towards the bottom end 49, and therefore improves the distribution of warm air.

In the abovementioned third embodiment whilst the nominal calculated diameter of the tubes varies it can be estimated that tubular portions 48 when inflated are about 153 mm diameter. The blanket in this embodiment having a length of about 1320 mm, and a width of about 950 mm.

Figure 5:
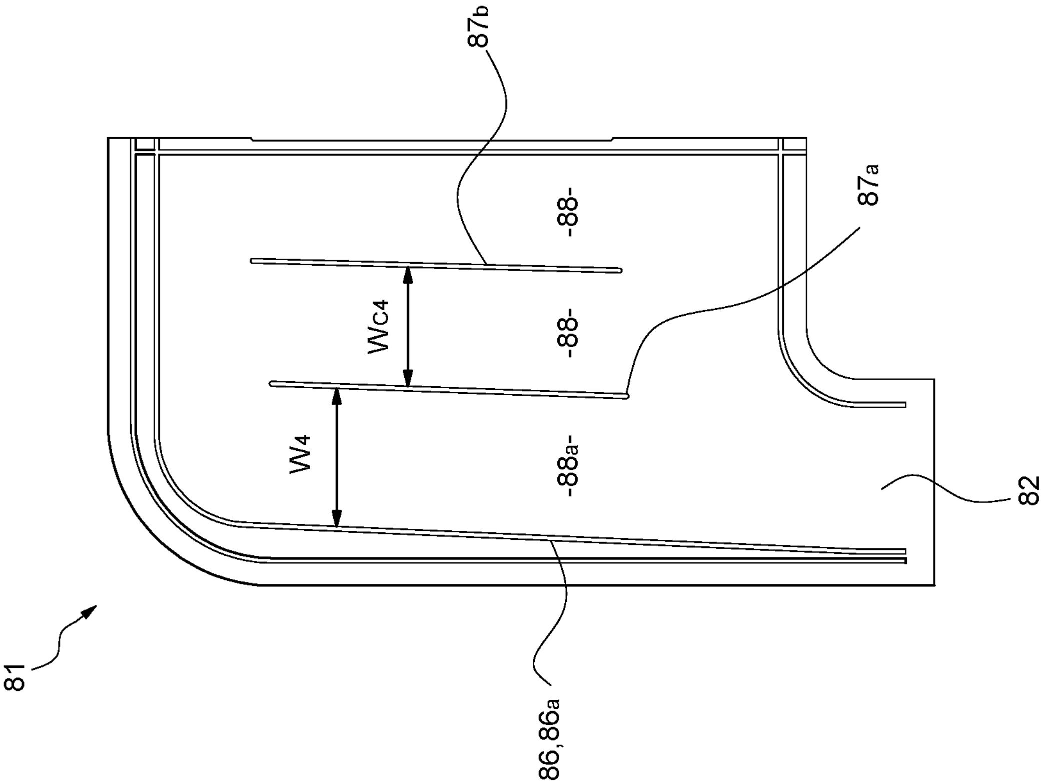
FIG. 5 is a plan view of an animal patient blanket in a fourth embodiment of the present invention.

FIG. 5 depicts a fourth embodiment of a blanket 81 which also is for use in veterinary medicine, and suited for being used for surgery of an exotic/small animal patient. This blanket 81 is a "half size" version of blanket 1 of the first embodiment.

The periphery 86 and heat welds 87 define sides of a plurality of tubular portions 88,88*a*. The sides defined by welds 47 and peripheral edges 86*a*,86*b* are non-parallel (or tapered), such that the tubular portions 88,88*a* each have wider openings at location nearer inlet 82 than they do near the opposed closed end 89 of blanket 81. In this embodiment the periphery edge 86*b* is substantially parallel to the longitudinal axis of blanket 1. The peripheral edge 86*a* is skewed at two and a half (2.5) degrees to periphery edge 86*b*, and side 87*b* is skewed at one and a half (1.5) degrees to periphery edge 86*b*, whilst side 87*a* is skewed at about two degrees to periphery 86*b*.

Tubular portion 88*a* has a width $W_4$ that is about ten percent wider than the width $W_{C4}$ of tubular portions 88.

Blanket 81 is also provided with a manifold 90. The length $L_{M4}$ of manifold 90 between the central open first ends of tubular portions 88 preferably should not be less than 20% the length of blanket 20.

In the abovementioned fourth embodiment whilst the nominal calculated diameter of the tubes varies it can be estimated that tubular portions 8 when inflated are about 145 mm diameter. The blanket in this embodiment having a length (from inlet end to closed end) of about 850 mm, and a width of about 438 mm.

Figure 6:
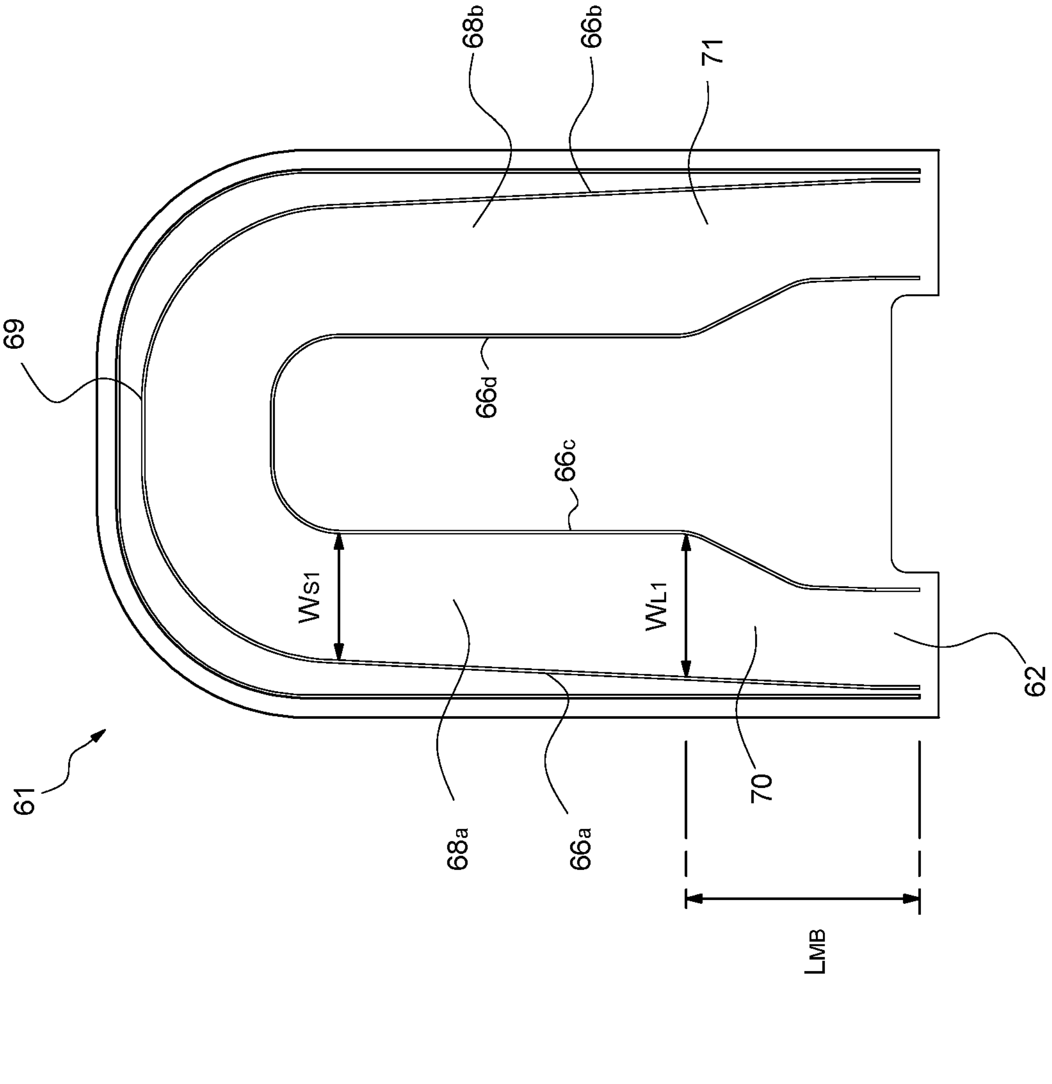
FIG. 6 is a plan view of a surgical animal patient blanket in a fifth embodiment of the present invention.

FIG. 6 depicts a fifth embodiment of a blanket 81 which also is for use in veterinary medicine, and suited being used for surgery of cat or small dog patient. Blanket 61 is substantially U-shaped and has an inlet 62 at a free end thereof. Blanket 61, like blanket 1 of the first embodiment, is provided with a hollow space which in use is connected to a blower heating unit (not shown), via inlet 62.

Also like blanket 1, blanket 61 is manufactured by heat welding two layers together, the second layer being made of porous material. The U-shape of blanket 61 made up of two elongate tubular portions 68*a*,68*b* fluidally interconnected by tubular bend portion 69. The peripheral sides 66*a*, 66*c* and 66*b*, 66*d* make up the sides of the respective elongate tubular portions 48*a*,48*b*.

Disposed immediately adjacent said inlet 62 is flared manifold 70 which transitions from said inlet 62 to first tubular portion 48*a*.

The respective sides 66*a*,66*c* are non-parallel (or tapered), such that first tubular portion 68*a* has a wider opening at location nearer manifold 50 and inlet 62 than it does near the opposed tubular bend portion 69. This means the width dimension $W_{L1}$ of first tubular portion 68*a* near the inlet/manifold end of blanket 61 is larger than the width dimension $W_{S1}$ near tubular bend 69. In this embodiment peripheral edge 66*a*,66*b* are each skewed 2 degrees to the longitudinal.

In this embodiment the tubular bend (or gallery) 69 has a diameter same as that of the tubular portions 68*a*,68*b* at $W_{S1}$.

The length $L_{MB}$ of manifold 70 between the end of first tubular portion 68*a* and inlet 62 should preferably not be less than 20% the length of blanket 61.

In the abovementioned embodiment whilst the nominal calculated diameter of the tubular portion 68*a* varies it can be estimated to be about 150 mm diameter, whilst the inlet manifold at $W_{L1}$ is about 190 mm, its nominal calculated diameter is about 171 mm, thus making it about 14% greater than the nominal calculated diameter of the tube 68*a*.

The width of tubular bend 69 has a radius sufficient to reduce kinking and its diameter remains substantially constant from tubular portion 68*a* to tubular portion 68*b*.

Second tubular portion 68*b*, like that of tubular portion also has non-parallel (or tapered) sides with the width closer to tubular bend 69 smaller than the width as it approaches flared portion 71 (similar to manifold 70).

Please note that all five abovementioned embodiments are described with reference to blankets for use in veterinary applications, however it should be understood the invention is also applicable for blankets used with human patients. It is also be understood that the sizes and dimensions may differ from those shown for different sized animals, such as for example large dogs and humans.

The terms "comprising" and "including" (and their grammatical variations) as used herein are used in an inclusive sense and not in the exclusive sense of "consisting only of".

The invention claimed is:

1. A veterinary patient warming blanket for placement in an animal cage for post operative warming comprising at least two layers capable of forming a hollow air space between said two layers for receiving warm air blown from a heating unit via an inlet port at or near an end of said blanket, said two layers being arranged so that said hollow air space forms a plurality of adjacent tubular portions disposed longitudinally within said blanket fluidally in communication with each other, and one of said two layers has at least a portion of its surface formed of porous material so that warmed air is delivered to said patient by gentle diffusion through said porous material, wherein each said tubular portion has tapered sides formed by continuous welds between said at least two layers such that said sides of each said tubular portion are further apart from each other at a first end of each said tubular portion closer to said inlet port than at a second end of each said tubular portion remote from said inlet port and a manifold is disposed between said inlet port and said first end of each said tubular portion, and at least one side of said tapered sides of each said tubular portion is skewed in a range of 1.5 to 2.5 degrees to the longitudinal axis.

2. A veterinary patient warming blanket as claimed in claim 1, wherein said plurality of adjacent tubular portions comprises two opposed outermost tubular portions that have a width wider than the tubular portions between them.

3. A veterinary patient warming blanket as claimed in claim 2 wherein two opposed outermost tubular portions are about ten percent larger in width than the adjacent tubular portions.

4. A veterinary patient warming blanket as claimed in claim 2, wherein said first ends of said tubular portions are staggered relative to each other.

5. A veterinary patient warming blanket as claimed in claim 4, wherein said staggered first ends of said tubular portions are staggered such that centrally disposed tubular portions have first ends longitudinally further away from said inlet port than adjacent tubular portions disposed on either side thereof.

6. A veterinary patient warming blanket as claimed in claim 2, wherein said plurality of adjacent tubular portions comprises centrally disposed tubular portions having first ends longitudinally further away from said inlet port than said two opposed outermost tubular portions.

7. A veterinary patient warming blanket for placement in a single animal cage for post operative warming, comprising at least two layers capable of forming a hollow air space between said two layers for receiving warm air blown from a heating unit via an inlet port at or near an end of said blanket, said two layers being arranged so that said hollow air space forms a plurality of adjacent tubular portions disposed longitudinally within said blanket fluidally in communication with each other, and one of said two layers has at least a portion of its surface formed of porous material so that warmed air is delivered to said patient by gentle diffusion through said porous material, wherein each said tubular portion has tapered sides formed by continuous welds between said at least two layers such that said sides of each said tubular portion are further apart from each other at a first end of each said tubular portion closer to said inlet port than at a second end of each said tubular portion remote from said inlet port and a manifold is disposed between said inlet port and said first end of each said tubular portion, and at least one side of said tapered sides of each said tubular portion is skewed in a range of 1.5 to 2.5 degrees to the longitudinal axis, and said plurality of adjacent tubular portions comprises two opposed outermost tubular portions that have a width about ten percent wider than the tubular portions disposed between them, and a gallery is disposed at a bottom end of said blanket near said second ends of said tubular portions and said gallery is in fluid communication with said manifold, and said gallery has a width between said bottom end and said second ends of said tubular portions which is no less than the ten percent the total length of the blanket.

* * * * *